United States Patent
Holmes et al.

(10) Patent No.: US 10,583,471 B2
(45) Date of Patent: Mar. 10, 2020

(54) NEURO-CHEMICAL SENSOR WITH INHIBITION OF FOULING ON NANO-ELECTRODE

(71) Applicant: INTERNATIONAL BUSINESS MACHINES CORPORATION, Armonk, NY (US)

(72) Inventors: Steven J. Holmes, Yorktown Heights, NY (US); Emily R. Kinser, Poughkeepsie, NY (US); Qinghuang Lin, Yorktown Heights, NY (US); Nathan P. Marchack, New York, NY (US); Roy R. Yu, Poughkeepsie, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 261 days.

(21) Appl. No.: 15/810,483

(22) Filed: Nov. 13, 2017

(65) Prior Publication Data
US 2018/0339321 A1 Nov. 29, 2018

Related U.S. Application Data

(63) Continuation of application No. 15/602,363, filed on May 23, 2017.

(51) Int. Cl.
*B08B 17/02* (2006.01)
*A61B 5/00* (2006.01)
(Continued)

(52) U.S. Cl.
CPC .......... *B08B 17/02* (2013.01); *A61B 5/04001* (2013.01); *A61B 5/4839* (2013.01);
(Continued)

(58) Field of Classification Search
CPC .......... B82Y 5/00; B82Y 15/00; B82Y 40/00; A61B 5/04001; A61B 5/4839;
(Continued)

(56) References Cited

U.S. PATENT DOCUMENTS 8,003,192 B2  8/2011  Hong et al.
8,263,002 B1  9/2012  Chow et al.
(Continued)

OTHER PUBLICATIONS

Huang, Y. et al., "Electrical stimulation elicits neural stem cells activation: new perspectives in CNS repair" Front. Hum. Neurosci. (Oct. 2015) pp. 1-9, vol. 9, Article 586.
(Continued)

*Primary Examiner* — Peter Dungba Vo
*Assistant Examiner* — Joshua D Anderson
(74) *Attorney, Agent, or Firm* — Tutunjian & Bitetto, P.C.; L. Jeffrey Kelly

(57) ABSTRACT

A biosensor includes an array of metal nanorods formed on a substrate. An electropolymerized conductor is formed over tops of a portion of the nanorods to form a reservoir between the electropolymerized conductor and the substrate. The electropolymerized conductor includes pores that open and close responsively to electrical signals applied to the nanorods. A dispensing material is loaded in the reservoir to be dispersed in accordance with open pores.

10 Claims, 11 Drawing Sheets

(51) Int. Cl.
  *A61B 5/04* (2006.01)
  *B08B 17/06* (2006.01)
  *B82Y 15/00* (2011.01)
  *B82Y 40/00* (2011.01)

(52) U.S. Cl.
  CPC .... *B08B 17/065* (2013.01); *A61B 2562/0209* (2013.01); *A61B 2562/0285* (2013.01); *A61B 2562/046* (2013.01); *A61B 2562/125* (2013.01); *B82Y 15/00* (2013.01); *B82Y 40/00* (2013.01)

(58) Field of Classification Search
  CPC ...... A61B 2562/0209; A61B 2562/028; A61B 2562/0285; A61B 2562/046; A61B 2562/12; A61B 2562/125; A61B 2562/245; A61M 31/002; B81C 1/0015; B81C 1/00087; B81C 1/00111; B81C 1/00119; B81C 1/00158
  See application file for complete search history.

(56) References Cited

U.S. PATENT DOCUMENTS

| 9,070,492 | B2 | 6/2015 | Yarmush et al. | |
|---|---|---|---|---|
| 2006/0189018 | A1 | 8/2006 | Yi et al. | |
| 2010/0233226 | A1* | 9/2010 | Ferain | A61K 9/0009 424/422 |
| 2012/0088994 | A1* | 4/2012 | Bode | A61B 5/14503 600/345 |
| 2012/0263793 | A1 | 10/2012 | Vitaliano | |
| 2014/0330244 | A1 | 11/2014 | Hyde et al. | |
| 2014/0336487 | A1* | 11/2014 | Wang | A61B 5/685 600/352 |
| 2015/0032137 | A1 | 1/2015 | Wagner et al. | |

OTHER PUBLICATIONS

Office Action issued in U.S. Appl. No. 15/811,023 dated Apr. 16, 2019, 9 pages.

Beebe, S.J., Nanosecond pulsed electric field (nsPEF) effects on cells and tissues: apoptosis induction and tumor growth inhibition IEEE Transactions on Plasma Science (Feb. 2002) pp. 286-292, vol. 30, No. 1.

Jeon, G. et al., "Electrically Actuatable Smart Nanoporous Membrane for Pulsatile Drug Release" Nano Letters (Jan. 2011) pp. 1284-1288, vol. 11.

List of IBM Patents or Patent Applications Treated as Related dated Nov. 13, 2017, 2 pages.

U.S. Office Action issued in U.S. Appl. No. 15/602,363, dated May 16, 2019, pp. 1-18.

Gu, Yan, et al., "Understanding nanoparticle drug delivery from rotational dynamics and behaviors of functionalized gold nanorods on live cell membranes," Biophys. J, 2011, pp. 473a-473a, 100,3.

Kim, Kibeom, et al., "Externaly controlled drug release using a gold nanorod contained composite membrane," Nanoscale, 2016, pp. 11949-11955, 8.

U.S. Final Office Action issued in U.S. Appl. No. 15/602,363, dated Oct. 21, 2019, 14 pages.

* cited by examiner

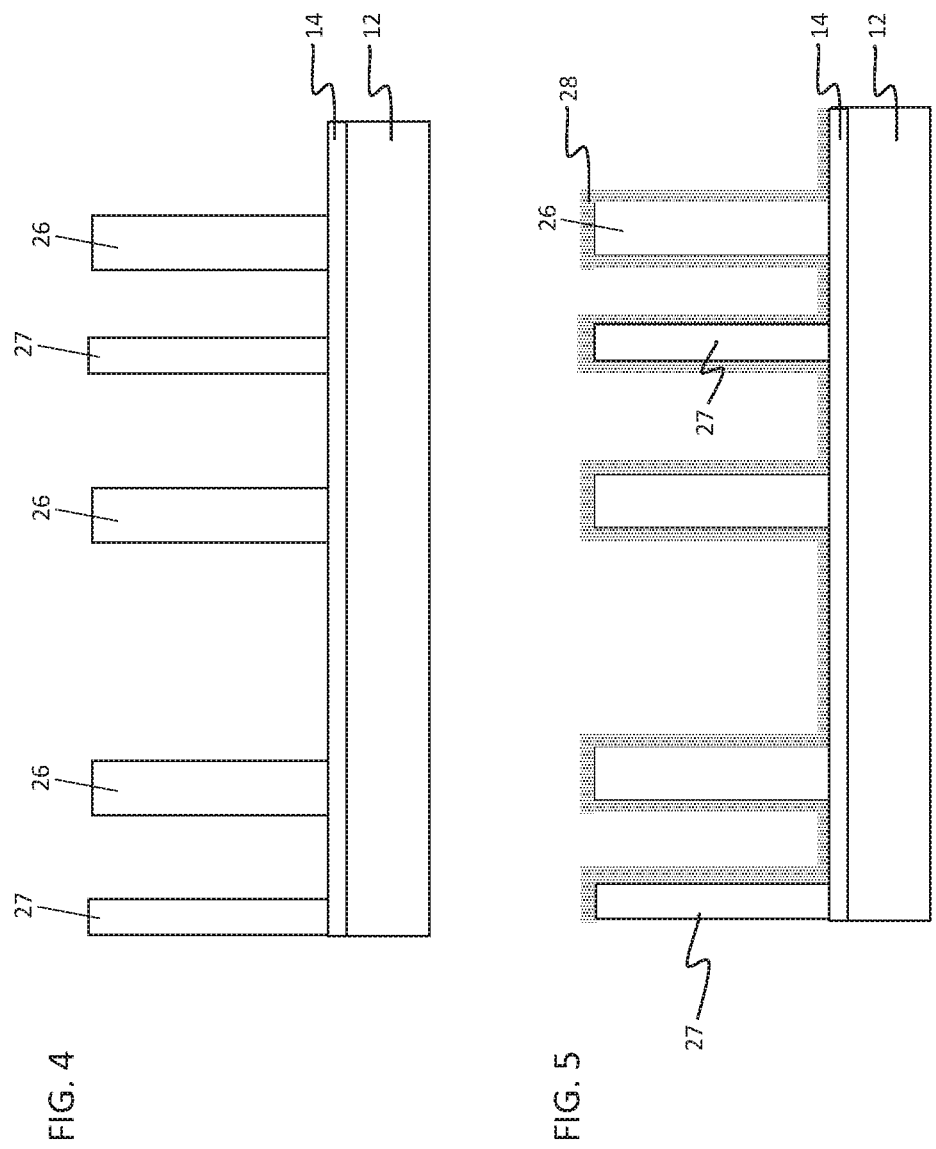

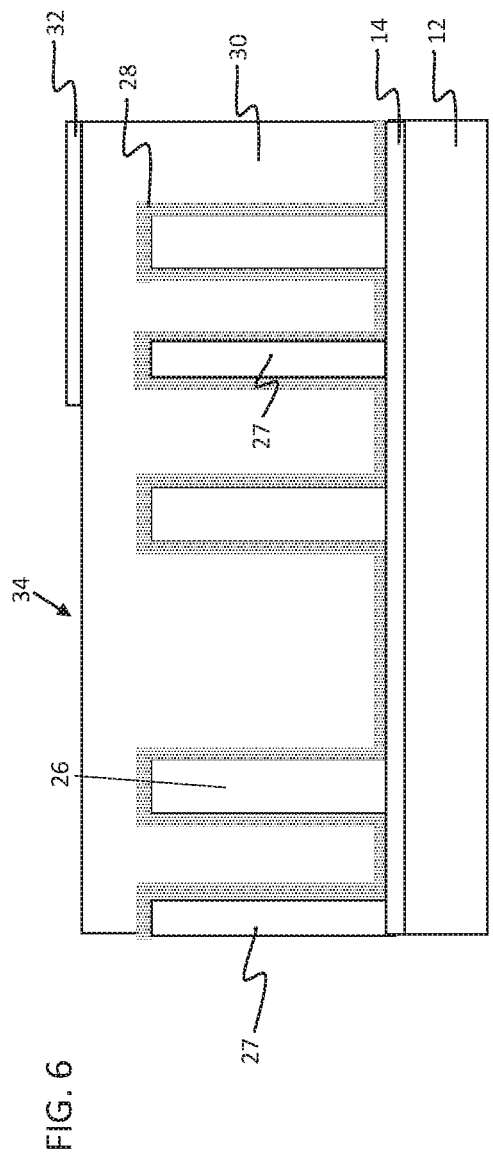
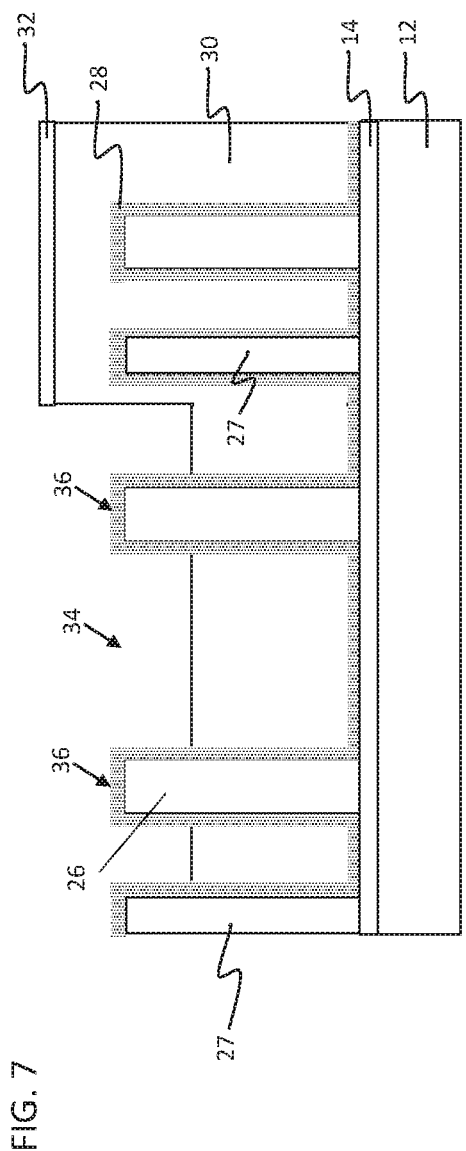

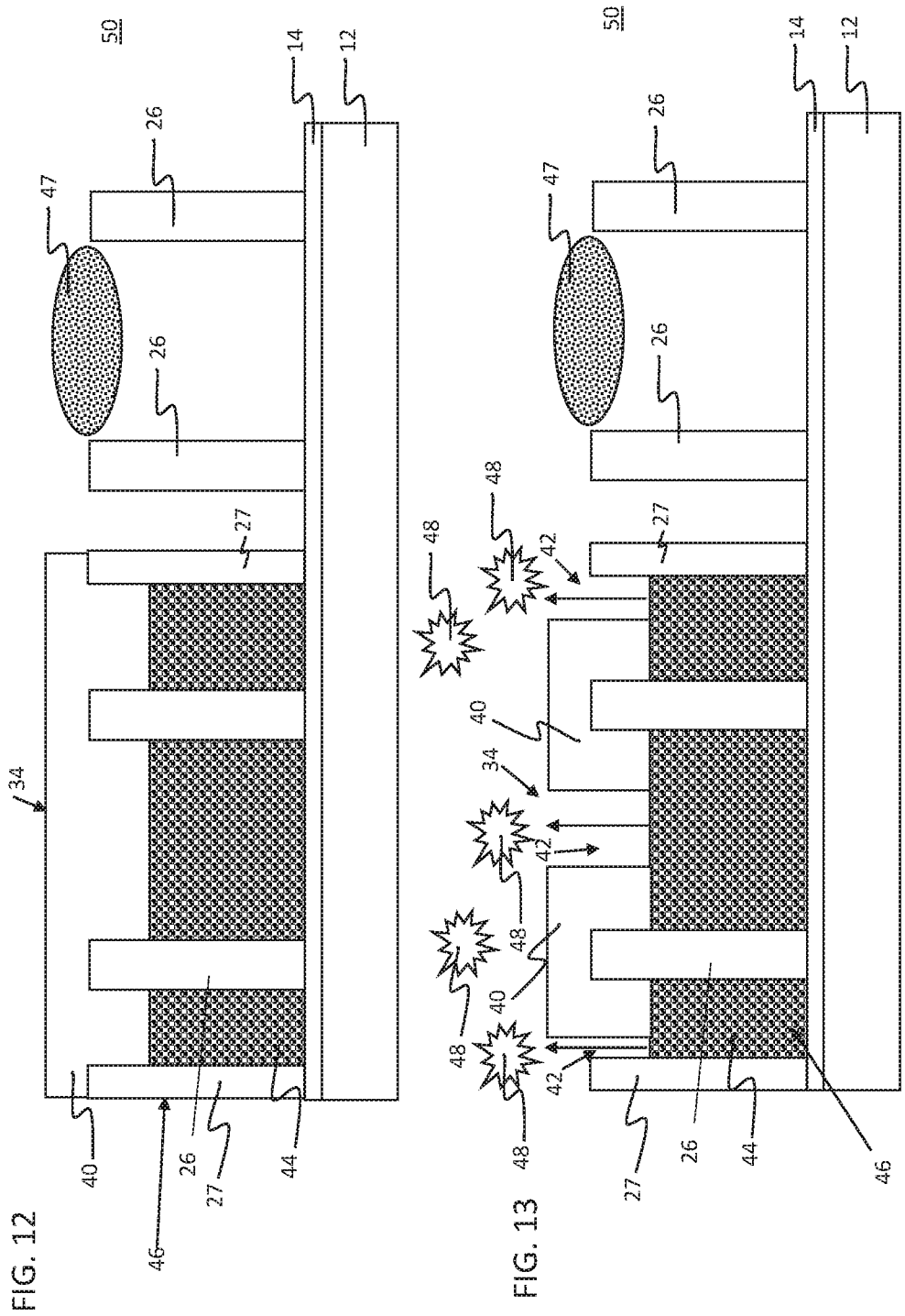

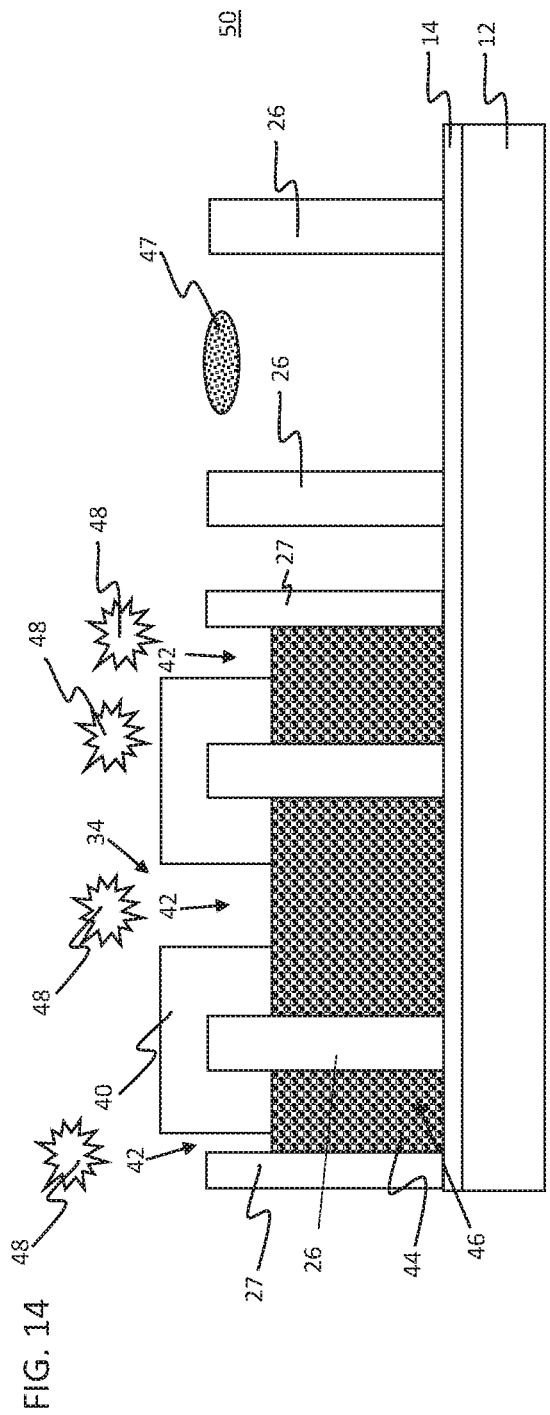

NEURO-CHEMICAL SENSOR WITH INHIBITION OF FOULING ON NANO-ELECTRODE

BACKGROUND

Technical Field

The present invention generally relates to biosensing devices, and more particularly to devices and methods to control molecular interactions at a device electrode by releasing inhibitors to prevent biofouling and/or to release growth factor to control cell growth.

Description of the Related Art

Biosensors can employ electrodes to measure properties of materials or to attract a substance being measuring or sensed. Electrodes employed on biosensors need protection to prevent competing molecules from reacting at the electrodes. Biosensors are useful for detection of neural activity, such as voltage changes around active neurons or the concentration levels of neurotransmitters. However, the lifetime of these biosensors in vivo can be short, due to fouling of the electrodes by accumulation of cellular materials or direct attack by the immune system on the biosensor.

SUMMARY

In accordance with an embodiment of the present invention, a biosensor includes an array of metal nanorods formed on a substrate. An electropolymerized conductor is formed over tops of at least a portion of the nanorods to form a reservoir between the electropolymerized conductor and the substrate. The electropolymerized conductor includes pores that open and close responsively to electrical signals applied to the nanorods. A dispensing material is loaded in the reservoir to be dispersed in accordance with open pores.

Another biosensor includes an array of metal nanorods formed on a substrate, the array or metal nanorods being grouped into a first region and a second region. The first region includes a first spacing between the nanorods such that upon activation an electric field inconsistent with cell activity is achieved. The second region includes a second spacing between the nanorods such that upon activation an electric field consistent with cell activity is achieved.

A method for fabricating a biosensor includes forming nanorods on a metal layer; forming a conformal layer over the nanorods; recessing the conformal layer on at least a portion of the nanorods; electropolymerizing a conductor on tops of nanorods exposed by recessing to form a reservoir between an electropolymerized conductor and the metal layer, the electropolymerized conductor including pores that open and close responsively to electrical signals applied to the nanorods; and loading a dispensing material to be dispersed in the reservoir in accordance with open pores.

These and other features and advantages will become apparent from the following detailed description of illustrative embodiments thereof, which is to be read in connection with the accompanying drawings.

BRIEF DESCRIPTION OF THE DRAWINGS

The following description will provide details of preferred embodiments with reference to the following figures wherein:

FIG. 4 is a cross-sectional view showing a new cross-section with three nanorods and two encapsulation walls formed on a substrate in accordance with an embodiment of the present invention;

FIG. 5 is a cross-sectional view showing the substrate of FIG. 4 having an atomic layer deposited coating formed on the metal layer, the nanorods and the encapsulation wall in accordance with an embodiment of the present invention;

FIG. 6 is a cross-sectional view showing the substrate of FIG. 5 having another organic planarizing layer formed and a hardmask patterned thereon in accordance with an embodiment of the present invention;

FIG. 7 is a cross-sectional view showing the substrate of FIG. 6 having the organic planarizing layer recessed to expose coated nanorods and the encapsulation wall in accordance with the patterned hardmask in accordance with an embodiment of the present invention;

FIG. 12 is a cross-sectional view showing the substrate of FIG. 11 being deployed in vivo with the dispensing material loaded and cells interacting with the device in accordance with an embodiment of the present invention;

FIG. 13 is a cross-sectional view showing the substrate of FIG. 12 having the dispensing material deployed through open pores in the electropolymerized conductor in accordance with an embodiment of the present invention;

FIG. 14 is a cross-sectional view showing the substrate of FIG. 13 with cells reduced or eliminated from the device in accordance with an embodiment of the present invention;

DETAILED DESCRIPTION

Figure 1:
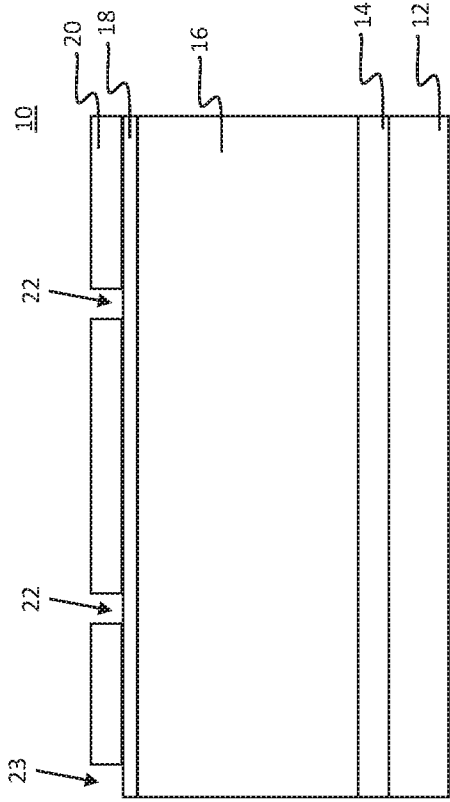
FIG. 1 is a cross-sectional view showing a substrate having a metal layer, organic planarizing layer, hard mask layer and patterned resist formed thereon for forming nanorods and an encapsulation wall in accordance with an embodiment of the present invention.

In accordance with embodiments of the present invention, biosensors are employed for measuring the presence of one or more materials in the vicinity or in contact with the biosensors. In useful embodiments, a substrate having electronics or connections to electronics can include one or more nanorods. The nanorods can include inert metals, such as Pt or the like. The nanorods are vertically disposed and have a diameter or transverse width of between about 20 nm to about 3 microns, preferably between about 100 nm to about 500 nm, although other useful sizes are contemplated. The nanorods can be arranged in an array or other configuration on the substrate to promote collection of materials or enhance the presence of materials.

In one embodiment, the biosensors employ electrodes for detection of neural activity, such as voltage changes around active neurons or concentration levels of neurotransmitters. These biosensors can include inhibition mechanisms to reduce or eliminate biofouling of the electrodes by accumulation of cellular materials or direct attack by the immune system on the biosensor. The electrodes are formed as nanorods that include the inhibition mechanism to remove or kill cells that interfere with sensing activities. The inhibition mechanism is employed using the electrodes to prevent competing molecules from reacting at the electrode.

In particularly useful embodiments, the inhibiting mechanism can inhibit or remove cellular growth from portions of a sensor or neuro sensor by applying appropriate chemicals or growth inhibitors in specific regions of the sensor. An implantable nano-device can address these problems by creating structures of electrically functional nano-pillar electrodes across a portion of a device substrate. In one embodiment, structures for nano-reservoirs of growth inhibitors can be provided with electrically controlled release in adjacent portions of the device substrate. The nano-device can be implanted into a desired region of neural tissue and an appropriate timed release of the growth inhibitors into the growth regions from the reservoirs on the nano-device can be activated. In other embodiments, the inhibition mechanisms can inhibit or remove cellular growth from portions of the neurosensor by applying voltage or electrical current in specific regions of the sensor. Combinations of these and other inhibition mechanisms can be employed together.

In other useful embodiments, a cell growth promoting mechanism can be employed to stimulate cellular growth from portions of a sensor or neurosensor by applying appropriate chemicals or growth promoters in specific regions of the sensor.

It is to be understood that aspects of the present invention will be described in terms of a given illustrative architecture; however, other architectures, structures, substrate materials and process features and steps can be varied within the scope of aspects of the present invention.

It will also be understood that when an element such as a layer, region or substrate is referred to as being "on" or "over" another element, it can be directly on the other element or intervening elements can also be present. In contrast, when an element is referred to as being "directly on" or "directly over" another element, there are no intervening elements present. It will also be understood that when an element is referred to as being "connected" or "coupled" to another element, it can be directly connected or coupled to the other element or intervening elements can be present. In contrast, when an element is referred to as being "directly connected" or "directly coupled" to another element, there are no intervening elements present.

The present embodiments can include a design for an integrated circuit chip, which can be created in a graphical computer programming language, and stored in a computer storage medium (such as a disk, tape, physical hard drive, or virtual hard drive such as in a storage access network). If the designer does not fabricate chips or the photolithographic masks used to fabricate chips, the designer can transmit the resulting design by physical means (e.g., by providing a copy of the storage medium storing the design) or electronically (e.g., through the Internet) to such entities, directly or indirectly. The stored design is then converted into the appropriate format (e.g., GDSII) for the fabrication of photolithographic masks, which typically include multiple copies of the chip design in question that are to be formed on a wafer. The photolithographic masks are utilized to define areas of the wafer (and/or the layers thereon) to be etched or otherwise processed.

Methods as described herein can be used in the fabrication of integrated circuit chips. The resulting integrated circuit chips can be distributed by the fabricator in raw wafer form (that is, as a single wafer that has multiple unpackaged chips), as a bare die, or in a packaged form. In the latter case, the chip is mounted in a single chip package (such as a plastic carrier, with leads that are affixed to a motherboard or other higher level carrier) or in a multichip package (such as a ceramic carrier that has either or both surface interconnections or buried interconnections). In any case, the chip is then integrated with other chips, discrete circuit elements, and/or other signal processing devices as part of either (a) an intermediate product, such as a motherboard, or (b) an end product.

It should also be understood that material compounds will be described in terms of listed elements, e.g., SiGe. These compounds include different proportions of the elements within the compound, e.g., SiGe includes $Si_xGe_{1-x}$ where x is less than or equal to 1, etc. In addition, other elements can be included in the compound and still function in accordance with the present principles. The compounds with additional elements will be referred to herein as alloys.

Reference in the specification to "one embodiment" or "an embodiment", as well as other variations thereof, means that a particular feature, structure, characteristic, and so forth described in connection with the embodiment is included in at least one embodiment. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This can be extended, as readily apparent by one of ordinary skill in this and related arts, for as many items listed.

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements and/or components, but do not preclude the presence or addition of one or more other features, integers, steps, operations, elements, components and/or groups thereof.

Spatially relative terms, such as "beneath," "below," "lower," "above," "upper," and the like, can be used herein for ease of description to describe one element's or feature's relationship to another element(s) or feature(s) as illustrated in the FIGs. It will be understood that the spatially relative terms are intended to encompass different orientations of the device in use or operation in addition to the orientation depicted in the FIGs. For example, if the device in the FIGs. is turned over, elements described as "below" or "beneath" other elements or features would then be oriented "above" the other elements or features. Thus, the term "below" can encompass both an orientation of above and below. The device can be otherwise oriented (rotated 90 degrees or at other orientations), and the spatially relative descriptors used herein can be interpreted accordingly. In addition, it will also be understood that when a layer is referred to as being "between" two layers, it can be the only layer between the two layers, or one or more intervening layers can also be present.

It will be understood that, although the terms first, second, etc. can be used herein to describe various elements, these elements should not be limited by these terms. These terms are only used to distinguish one element from another element. Thus, a first element discussed below could be termed a second element without departing from the scope of the present concept.

Referring now to the drawings in which like numerals represent the same or similar elements and initially to FIG. 1, a partially fabricated biosensor device 10 is shown in accordance with one embodiment. The device 10 includes a substrate 12 having one or more layers formed thereon. The substrate 12 can include any suitable substrate structure, e.g., a bulk semiconductor, a semiconductor-on-insulator (SOI) substrate, etc. In one example, the substrate 12 can include a silicon-containing material. Illustrative examples of Si-containing materials suitable for the substrate 12 can include, but are not limited to, Si, SiGe, SiGeC, SiC and multi-layers thereof. Although silicon is the predominantly used semiconductor material in wafer fabrication, alternative semiconductor materials can be employed as additional layers, such as, but not limited to, germanium, gallium arsenide, gallium nitride, silicon germanium, cadmium telluride, zinc selenide, etc.

Since the present embodiments provide a device that can work remotely, the device 10 can include a substrate having powered circuitry for controlling the functions of the device. In this way, the substrate 12 can include control circuitry fabricated using known semiconductor processing techniques. Components can include transistors, metal lines, capacitors, logic gates or any other electronic components that permit the control of the nanorods and other structures to be formed in subsequent steps. In one useful embodiment, bipolar junction transistors (BJT) can be employed in the circuitry formed in the substrate 12. BJT devices can be employed to generate sub-nanosecond pulsing, as will be described.

A metal layer 14 is deposited on the substrate 12 and can be employed with other components formed in the substrate 12 (e.g., as a metal layer). The metal layer 14 can include a conductive but relatively inert metal, such as, e.g., Pt, Au, Ag, Cu, Jr, Ru, Rh, Re, Os, Pd, and their oxides (e.g., $IrO_2$, RuOx, etc.), although other metals, metal oxides and their alloys can be employed. The metal layer 14 can be formed by deposition using a sputtering process, chemical vapor deposition (CVD) process, atomic layer deposition (ALD), a plating process or any other suitable deposition process.

In one embodiment, an organic planarizing layer (OPL) 16 is formed on the metal layer 14. The OPL 16 can be formed by a spin-on process or other deposition process. Other dielectric layers can also be employed.

An etch stop layer or hard mask 18 can be deposited over the OPL 16. In one embodiment the etch stop layer 18 can include a metal, such as, e.g., Ti, Ta, etc. or a metallic compound such as, e.g., TiN, TaN, SiARC (a silicon containing organic ARC layer), TiARC (a titanium ARC), etc. A resist layer 20 is formed on the etch stop layer or hard mask 18. The resist layer 20 can be spun on. The resist layer 20 is patterned to form openings 22 that will be employed to form nanorods and other openings 23 to form an encapsulation wall as will be described.

Figure 2:
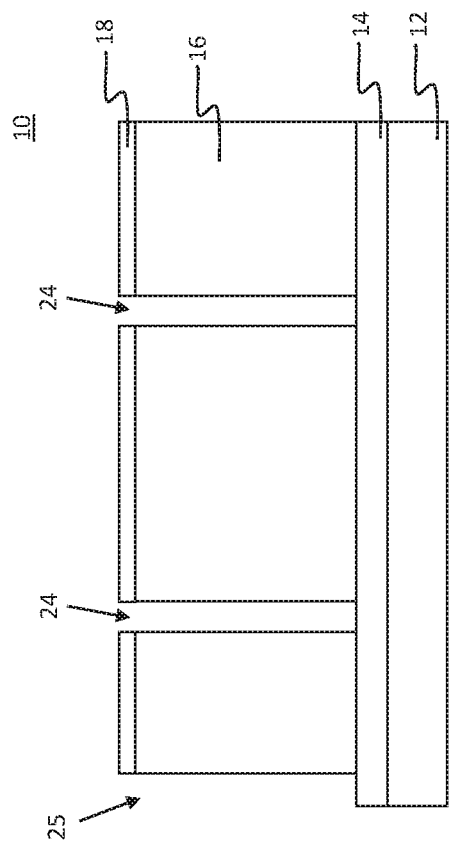
FIG. 2 is a cross-sectional view showing the substrate of FIG. 1 having the metal layer exposed by etching the organic planarizing layer in accordance with the hard mask layer and the patterned resist for forming nanorods and the encapsulation wall in accordance with an embodiment of the present invention.

Referring to FIG. 2, an etch process is performed to open up the etch stop layer 18. In one embodiment, a reactive ion etch (RIE) process can be performed to expose the OPL 16 through the openings 22 and 23 (FIG. 1). Then, a RIE is performed to etch through the OPL 16 to expose the metal layer 14 and form trenches 24 and 25 in accordance with the resist 20 and/or the etch stop layer or hard mask 18. The trenches 24 provide locations for the formation of nanorods and an encapsulation wall. The etch of OPL 16 should be minimized to maintain small critical dimensions (CDs) for the hole or trench 24 to be plated.

Figure 3:
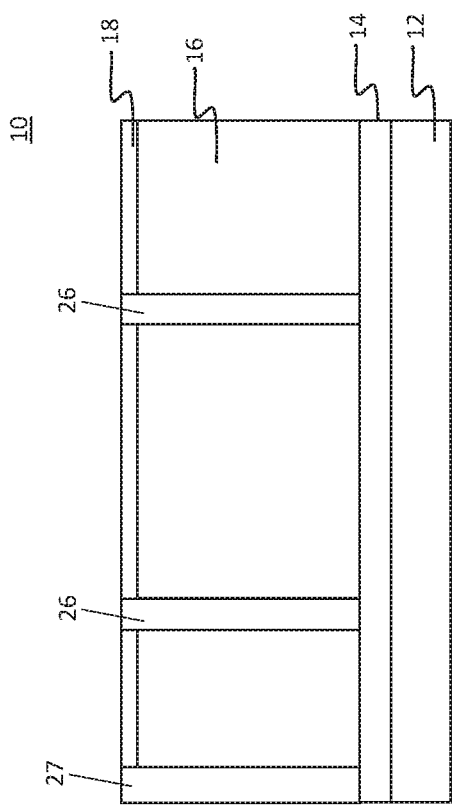
FIG. 3 is a cross-sectional view showing the substrate of FIG. 2 having nanorods and the encapsulation wall plated and connecting to the metal layer and planarized to the hard mask layer in accordance with an embodiment of the present invention.

Referring to FIG. 3, a metal deposition process is performed and can include a plating process, CVD, sputtering or the like. The metal of the deposition process preferably includes a same metal as employed in metal layer 14. In one particularly useful embodiment, the metal of layer 14 and the metal used in nanorods 26 and an encapsulation wall 27 can include, e.g., Pt, Au, Ag, Cu, Jr, Ru, Rh, Re, Os, Pd, and/or their oxides (e.g., $IrO_2$, RuOx, etc.), although other metals, metal oxides and their alloys can be employed. The nanorods 26 and the encapsulation wall 27 can be annealed with the OPL 16 present or with the OPL 16 removed. If the hard mask 18 includes, e.g., Ti or TiN, the hard mask 18 can be removed with hydrogen peroxide aqueous solution, or if it is Ti oxide or TiARC, it can be removed with diluted HF, as wet etching is simpler and easier to control than planarization processes such as, e.g., a chemical mechanical polish (CMP). However, a planarization process, such as, e.g., CMP, can be employed if other hard mask materials are employed. The hard mask 18 is removed down to the OPL 16. Then, the OPL 16 can be removed by a plasma strip, e.g., oxygen plasma, forming gas plasma, with a mild wet clean to remove residues.

The encapsulation wall 27 forms a closed shape formed from metal lines configured to permit the formation of a reservoir. The encapsulation wall 27 can have a thickness on the same order and the nanorods 26, although any suitable thickness can be employed. In one embodiment, the walls 27 form an open-topped polygonal structure (e.g., similar to an above-ground pool).

Referring to FIG. 4, after the removal of the OPL 16 and the anneal of the nanorods 26 and encapsulation wall 27, the nanorods 26 and the encapsulation wall 27 are ready for continued processing. The nanorods 26 can be arranged in any configuration suitable for creating a biosensor, e.g., an array with uniform or non-uniform spacings, etc. for chemical sensors, neurological implants or other applications.

Referring to FIG. 5, a coating 28 is formed over the nanorods 26, encapsulation wall 27 and metal layer 14. The coating 28 is formed using ALD, which can be processed to prepare a protective membrane on the electrodes. The membrane can include a $SiO_2$ film although other materials including organic dielectrics can be employed. In one embodiment, the coating can be formed by mixing ALD with aluminum, silicon or other materials, which can be formed in multiple layers. Each cycle of the ALD process can deposit a layer with an oxidation process thereafter to form a respective oxide (e.g., $SiO_2$ or $Al_2O_3$). In useful examples, the ALD reagent for forming Al can include $AlMe_3$ while the reagent for forming the $SiO_2$ can include $(Me_2N)_3SiH$ (where Me is a methyl group). The ALD process can include a plurality of cycles to deposit a plurality of layers. The plurality of layers can include a large number (e.g., two to several hundred). The plurality of layers form the coating 28, which can have a total thickness of between about 2 nm to about 50 nm. While other dimensions are contemplated, the coating 28 preferably includes a nanoscale thickness.

Referring to FIG. 6, another OPL 30 is formed over the coating 28. The OPL 30 can be spun-on although other formation processes can be employed. Another hardmask 32 is formed on the OPL 30. The hardmask 32 can include a metal, such as, e.g., Ti, Ta, etc. or a metallic compound such as, e.g., TiN, TaN, etc. A resist (not shown) can be employed in a lithographic patterning process to pattern the etch mask 32 and protect a portion of the etch mask 32 during an etch. The etch, e.g., RIE, removes the hardmask 32 from a region 34 to open the region 34 for a growth factor reservoir to be formed.

Referring to FIG. 7, the OPL 30 is recessed in the region 34 to expose tops 36 of the coating 28 over the nanorods 26 in the region 34. The recess process can include a RIE selective to the coating 28 and the hard mask 32.

Figure 8:
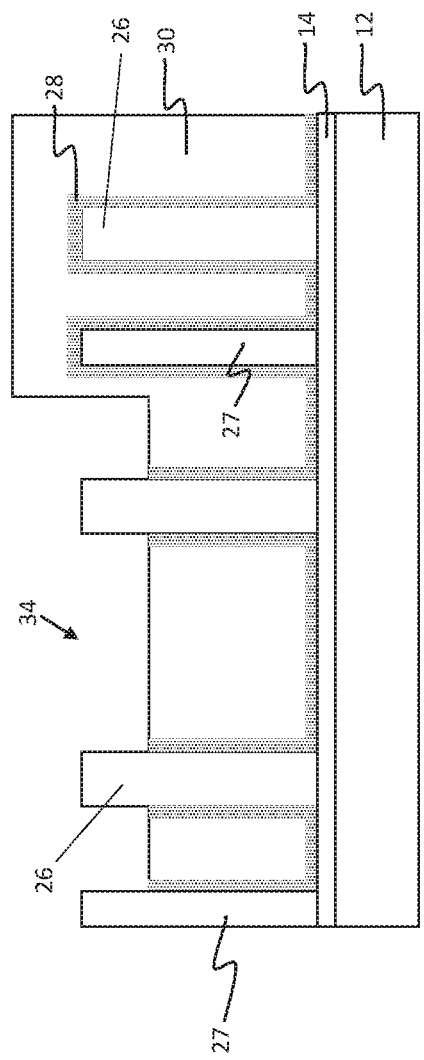
FIG. 8 is a cross-sectional view showing the substrate of FIG. 7 having the coating removed from the nanorods and the encapsulation wall that was exposed by the recess and having the patterned hardmask removed in accordance with an embodiment of the present invention.

Referring to FIG. 8, a wet etch process can be performed to wet etch coating 28 from the nanorods 26 and encapsulation wall 27 in the region 34. The wet can include, e.g., a diluted HF etch (DHF). Another wet etch can be performed to remove the hard mask 32 (FIG. 7) selectively relative to the nanorods 26 and the OPL 30. For example, if the hard mask 32 includes Ti, a wet etch with hydrogen peroxide ($H_2O_2$) can be employed to remove the hardmask.

Figure 9:
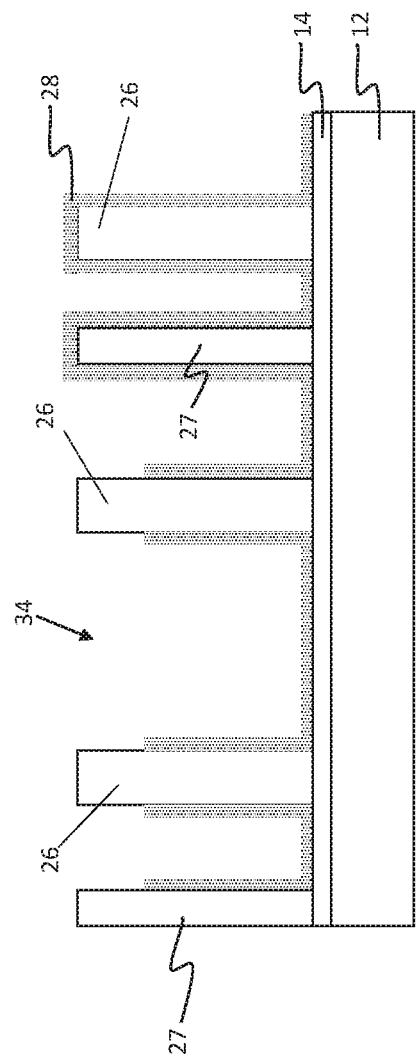
FIG. 9 is a cross-sectional view showing the substrate of FIG. 8 having the organic planarizing layer removed in accordance with an embodiment of the present invention.

Referring to FIG. 9, the OPL 30 is stripped to expose the coating 28 on the nanorods 26 and the encapsulation wall 27. The OPL 30 can be stripped using a plasma etch, such as, e.g., an $O_2$ plasma etch or $N_2/H_2$ plasma etch. The nanorods 26 which had coating 28 removed by, e.g., a wet etch previously, are exposed within the region 34.

Figure 10:
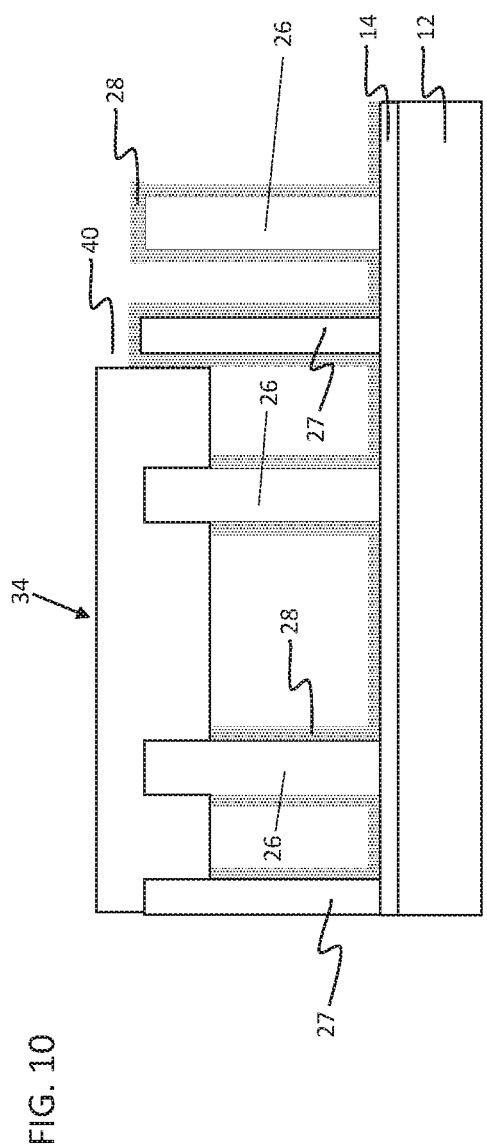
FIG. 10 is a cross-sectional view showing the substrate of FIG. 9 having an electropolymerized conductor formed on the exposed nanorods (and the encapsulation wall) in accordance with an embodiment of the present invention.

Referring to FIG. 10, an electropolymerization process is performed to grow a conductive porous polymer 40 on the exposed portions of the nanorods 26 and encapsulation wall 27 in the region 34. In one embodiment, the porous polymer 40 forms an electrically responsive nanoporous membrane based on polypyrrole doped with a dodecylbenzenesulfonate anion (PPy/DBS) that is electropolymerized on the nanorods 26.

Electropolymerization is the process by which a polymer is formed using electrical current. The electrical current can be provided through the exposed nanorods 26 in the presence of a polymer (e.g., polypyrrole in solution). Doping can occur in-situ or after formation with the absorption of an anion or other charged molecule. The porous polymer 40 includes a regular pore size. The porous polymer 40 is configured to provide a large volume change depending on its electrochemical state, and the pore size can be actuated electrically. The porous polymer 40 is formed in its oxidation state. The porous polymer 40 includes a thickness where pores formed therein include sufficient length to pass through the entire porous polymer layer.

The coating 28 is removed from remaining portions of the nanorods 26 and encapsulation wall 27 by a wet etch. The wet etch can include a diluted HF etch, although other etchants can be employed. Once formed, the porous polymer 40 can have its pores opened and closed in accordance with an electrical potential applied to the polymer 40 by nanorods 26.

Figure 11:
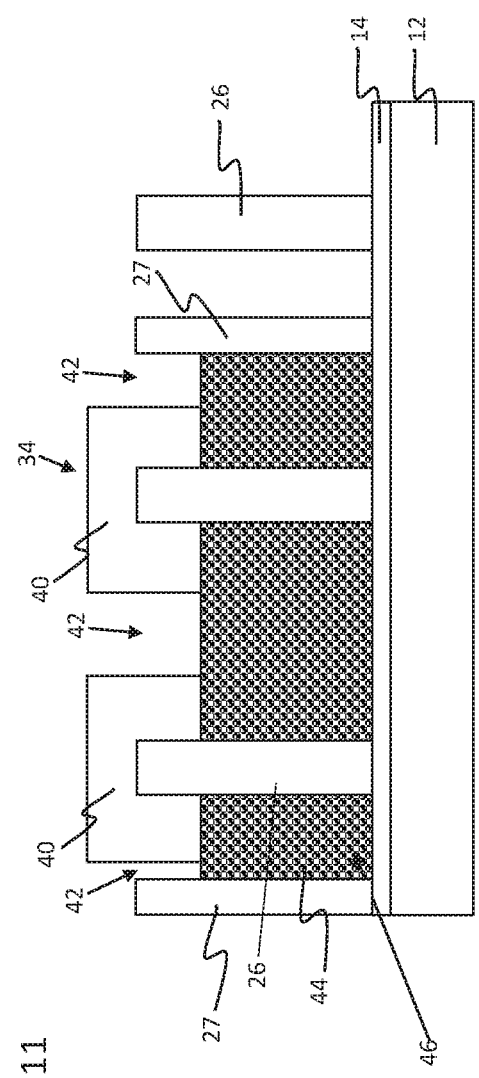
FIG. 11 is a cross-sectional view showing the substrate of FIG. 10 having pores of the electropolymerized conductor opened to load a dispensing material in to a reservoir in accordance with an embodiment of the present invention.

Referring to FIG. 11, a growth inhibitor (or growth promoter) reservoir 46 is formed using the encapsulation wall 27 between the polymer 40 and the metal layer 14. The polymer 40 can be electrically actuated to open pores 42 through the polymer 40, which switches to the polymer material's reduction state (as opposed to its oxidation state). The state changes can be made by a potential difference of between about 0.9 to about 1.2 volts applied to the nanorods 26. When the pores 42 are opened, a growth inhibiter 44 can be collected within the reservoir 46. The growth inhibitor 44 can include any useful chemical or reagent, e.g., chemotherapy drugs (e.g., cytotoxic agents, alkylating agents, anthracyclines, cytoskeletal disruptors, epothilones, histone deacetylase inhibitors, peptide antibiotics, retinoids, etc.), hormone species (e.g., somatostatin, etc.), other materials, or combinations. In alternate embodiments, a growth stimulator or promoter (44) can be loaded. The growth stimulator 44 can include any useful chemical or reagent, e.g., hormone species (e.g., steroids, etc.), metabolic stimulants, other materials, or combinations. Once growth inhibitor (or stimulator) 44 is loaded, the pores 42 of polymer 40 are closed by changing the voltage on the nanorods 26 (and/or the encapsulation walls 27).

Referring to FIG. 12, a device 50 can be placed in vivo by surgery or injection. As cells 47 interact with the surface of the device 50, the cells 47 can begin to grow or otherwise interfere with the operation of the device 50. For example, the device 50 can be placed in vivo to sense or measure concentrations of materials within the body. When cells 47 begin to affect function of the device 50, the growth inhibitor reservoir 46, which is loaded with growth inhibitor 44, can be selectively exposed to release growth inhibiter material. Electrodes (nanorods 26) in region 34 are activated to open from the closed position depicted in FIG. 12.

Referring to FIGS. 13 and 14, electrodes (nanorods 26) in region 34 are activated to open the pores 42 or the polymer 40 to an open position. This permits growth inhibitor 48 to be released through the pores 42. The growth inhibitor 48 includes a dosage that will provide biofouling inhibition without significant damage to other surrounding tissues. The growth inhibitor 48 interferes with growth of the cell or cells 47 reducing the size of the cell 47 and/or its influence on the device 50 as depicted in FIG. 14.

The opening of the pores 42 can be performed in a pulsatile (or on-demand) manner so that the release of growth inhibitor 48 can be carefully controlled. A switching time of a few seconds or less can be employed to provide local and on-demand delivery of the growth inhibitor 48. The pores 42 can be reclosed until activated at a later time to further inhibit biofouling. In alternate embodiments, a growth stimulator or promoter (44) can be deployed instead of the growth inhibitor to stimulate cell growth or to treat a wound or other tissue.

Figure 15:
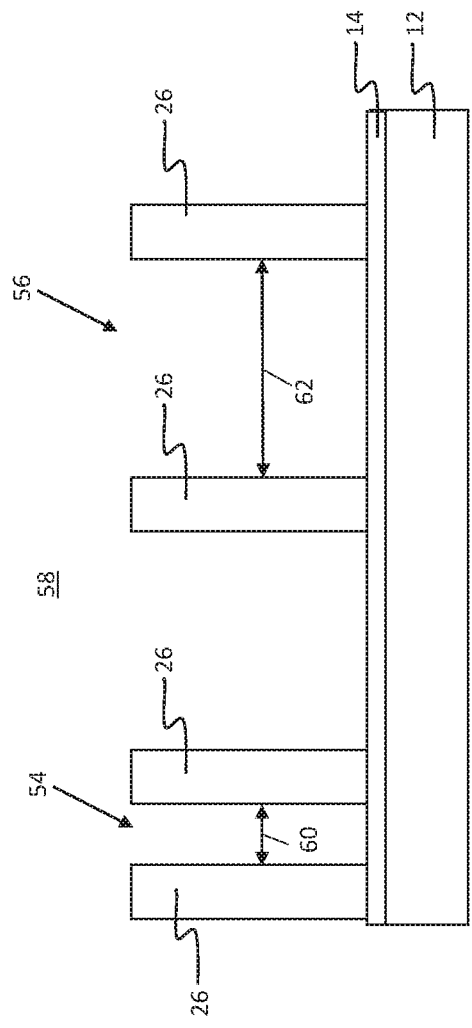
FIG. 15 is a cross-sectional view showing a substrate having nanorods spaced to produce different electric field intensities in different regions when activated in accordance with an embodiment of the present invention.

Referring to FIG. 15, in other embodiments, inhibitor mechanisms can employ the nanorods 26 to inhibit or remove cellular growth from portions of a device 58 (e.g., a neurosensor) by applying appropriate voltage or electrical current in specific regions of the device 58. The device can include one or more regions 54, 56.

The device 58, e.g., a biosensors, can incorporate a combination of active sensor regions 56 and also regions 54 of cell growth inhibition. The nanorods 26 in region 54 can, for example, have a narrow spacing 60 (e.g., between about 20 nm-1000 nm), such that a common voltage applied to all nanorods 26 results in a higher electric field intensity between the narrower spacings 60. The electric field intensity can be controlled by adjusting voltage (e.g., between about 0.5 volts to about 100 volts (or higher)) and current conditions using circuit components or controls integrated into the device 58. In useful embodiments, the nanorods 26 in region 54 can be subjected to nanosecond (e.g., 0.1 ns to about 500 ns) pulsed electric fields (nsPEF) which can induce apoptosis in cells.

It should be understood that electric field intensity can be adjusted in a plurality of ways. For example, the size, shape and density of the nanorods 26 can be controlled. In other embodiments, pulse shapes and pulse frequencies can be adjusted and controlled for pulsations of voltage or current to the nanorods. Other electric field intensity controls are also contemplated, e.g., nanorod coatings, such as, e.g., a porous protective coating, biofouling coating, electrical insulating layers, etc.

The biosensor regions 56 can have an increased spacing 62 to reduce electric field intensity to permit cell growth for measurement or sensing operations. In some embodiments, the biosensor regions 56 can be controlled to change from an active sensing region to a growth inhibition region using the voltage or current conditions as controlled by the circuit components or controls integrated into the device 58. In this way, regions or the entire sensor surface can be periodically cleansed of cellular material by appropriate control of voltage and current conditions.

The nanorods 26 can be formed at different pitches and configurations during the patterning process as depicted in FIG. 1. The nanorods 26 can be configured for specific tasks including protecting the device 58 from biofouling, to sense the presence of bio or chemical material and/or to treat specific diseases or enable sensor functionality.

Figure 16:
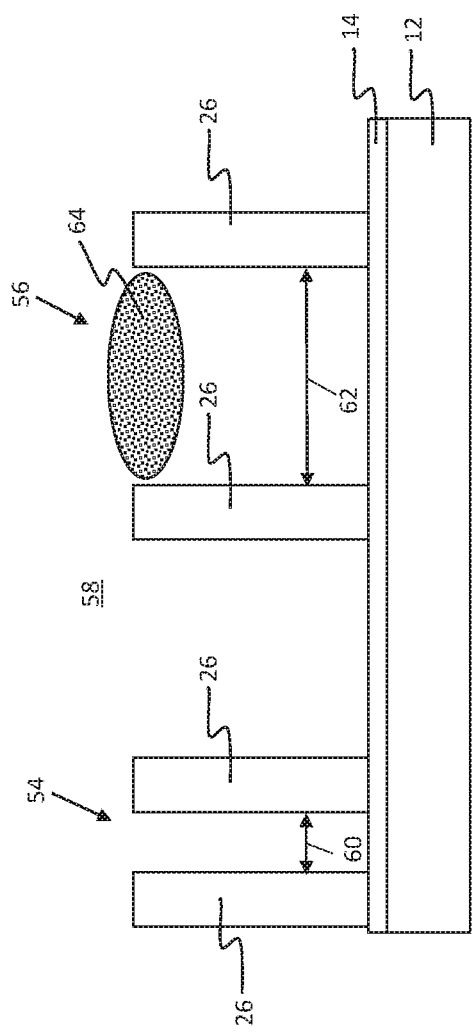
FIG. 16 is a cross-sectional view showing the substrate of FIG. 15 having different regions providing different functions in accordance with an embodiment of the present invention.

Referring to FIG. 16, in one embodiment, region 54 prevents or inhibits cellular growth while region 56 stimulates cell growth. For example, region 56 can permit electrical stimulation of neuro-stem cells 64, in place on the device 58. Cell 64 can be bound to nanorod electrodes 26 in region 56, which includes an electrical pulsation that stimulates cell growth. The cells 64 can be employed in a treatment program, e.g., in vivo. Therefore, depending on the application, growth inhibition or growth stimulation can be provided in accordance with the present embodiments depending on the electrical settings and environmental conditions created. An example of environmental conditions created for growth inhibition can include the introduction of biofouling reducing chemical or materials. An example of environmental conditions created for growth stimulation can include incorporating growth factors into the chemical storage region, rather than growth inhibitors, e.g., for a stem cell application.

Figure 17:
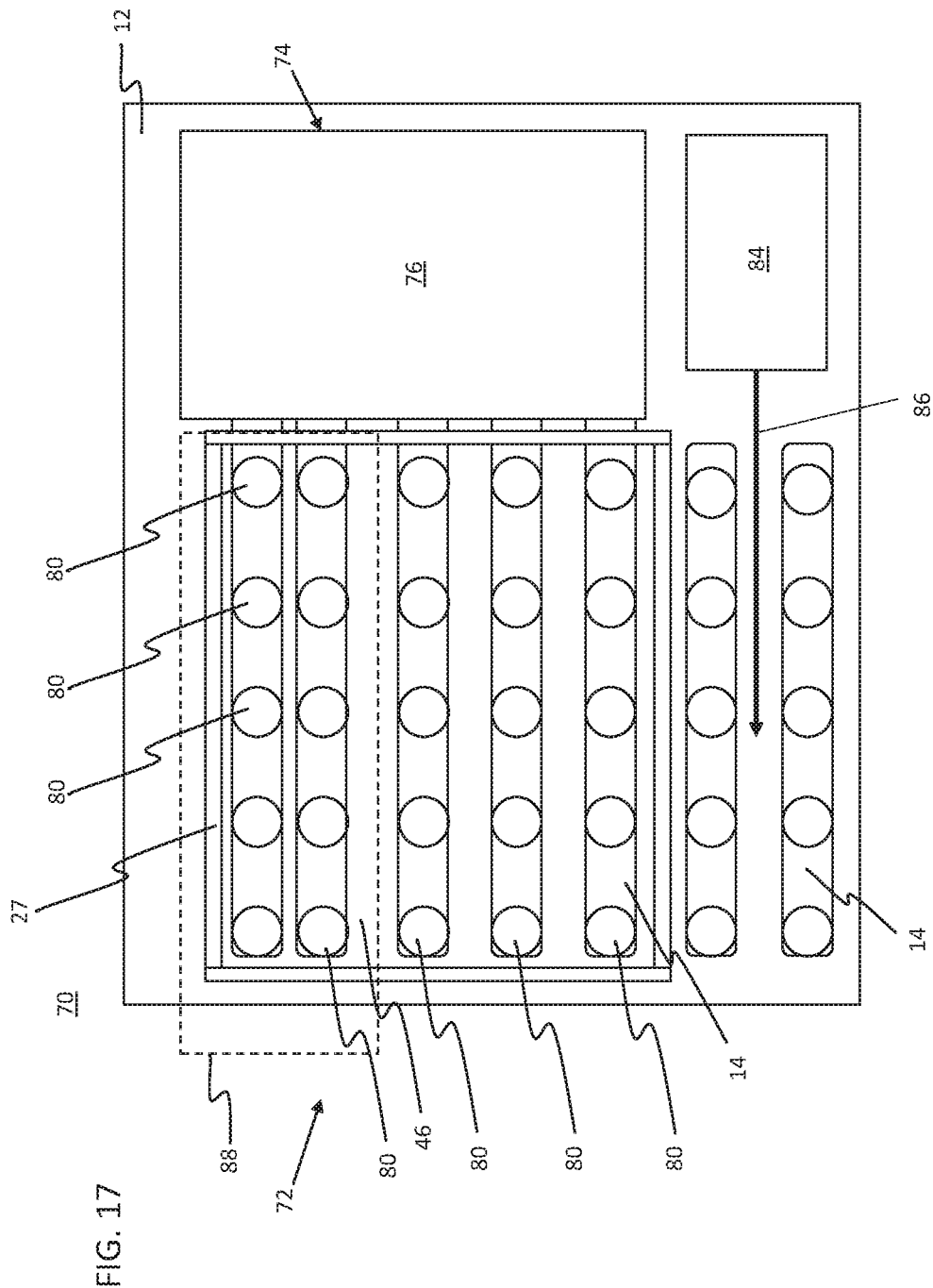
FIG. 17 is a plan schematic view showing a biosensor device having nanorods and circuits integrated on a substrate in accordance with an embodiment of the present invention.

Referring to FIG. 17, a device 70 for inhibiting biofouling or promoting growth is illustratively shown in accordance with one embodiment. The device 70 includes an array 72 of electrodes 80. The array 72 includes uniform spacings between electrodes 40; however, non-uniform spacings can be employed. An illustrative encapsulation wall 27 is shown to form a reservoir 46. A circuit 74 can include an array of transistors and/or other circuit components (e.g., integrated into the substrate 12) configured to activate or selectively activate electrodes. The circuit 74 can be integrated into the substrate 12 using semiconductor processing techniques. The circuit 74 can include a high voltage power source, e.g., if the device 70 is implantable in the body. Alternatively, the circuit 74 can connect to a separate external power source.

The circuit 74 can be controlled using a controller circuit 76 that generates signals to control which electrodes 80 are activated. The high voltage (e.g., 0.5 to 100 volts) can be programmed to activate the electrodes 80 using a patterned metal layer 14 to connect to the electrodes 80 in localized areas to prevent cell growth over specific regions of the array 72 or the whole array 72. The activation of the electrodes can prevent cell growth or selectively kill cells in these regions or parts of cells in the region. The activation of the electrodes can also promote cell growth or selectively grow cells in these regions or parts of cells in the region.

Device 70 can also include a biosensor that employs biological recognition properties for selective detection of various analytes or biomolecules. The biosensor 70 can generate a signal or signals that quantitatively relate to a concentration of the analyte on or near the electrodes 80. To achieve a quantitative signal, a recognition molecule or combination of molecules can be immobilized at the electrodes 80, which convert the biological recognition event into a quantitative response.

In some embodiments, the nanorod electrodes 80 can produce electrical fields for inhibiting biofouling, stimulating cell growth, releasing drugs or growth inhibitors or combinations of these tasks. In another embodiment, a radiation source 84, such as, e.g., a laser, nuclear radiation source or the like can direct radiation 86 to selectively kill cells in specific regions of the device 70. The device 70 can oscillate between measuring cycles and cycles to inhibit biofouling using, e.g., high voltage pulses or the like.

Device 70 can include regions with different spacings between nanorods 80 (e.g., region 88). Device 70 can include different biofouling inhibiting mechanisms and can include electrical based systems using spacings and electrical pulses to cause cell reduction or death and/or promoter/inhibiter dispensing mechanisms or combinations of these or other mechanisms. The device 70 can be made disposable after use. The substrate 12 and other components can be coated or shielded to prevent contamination to the host from materials of the device 70.

Figure 18:
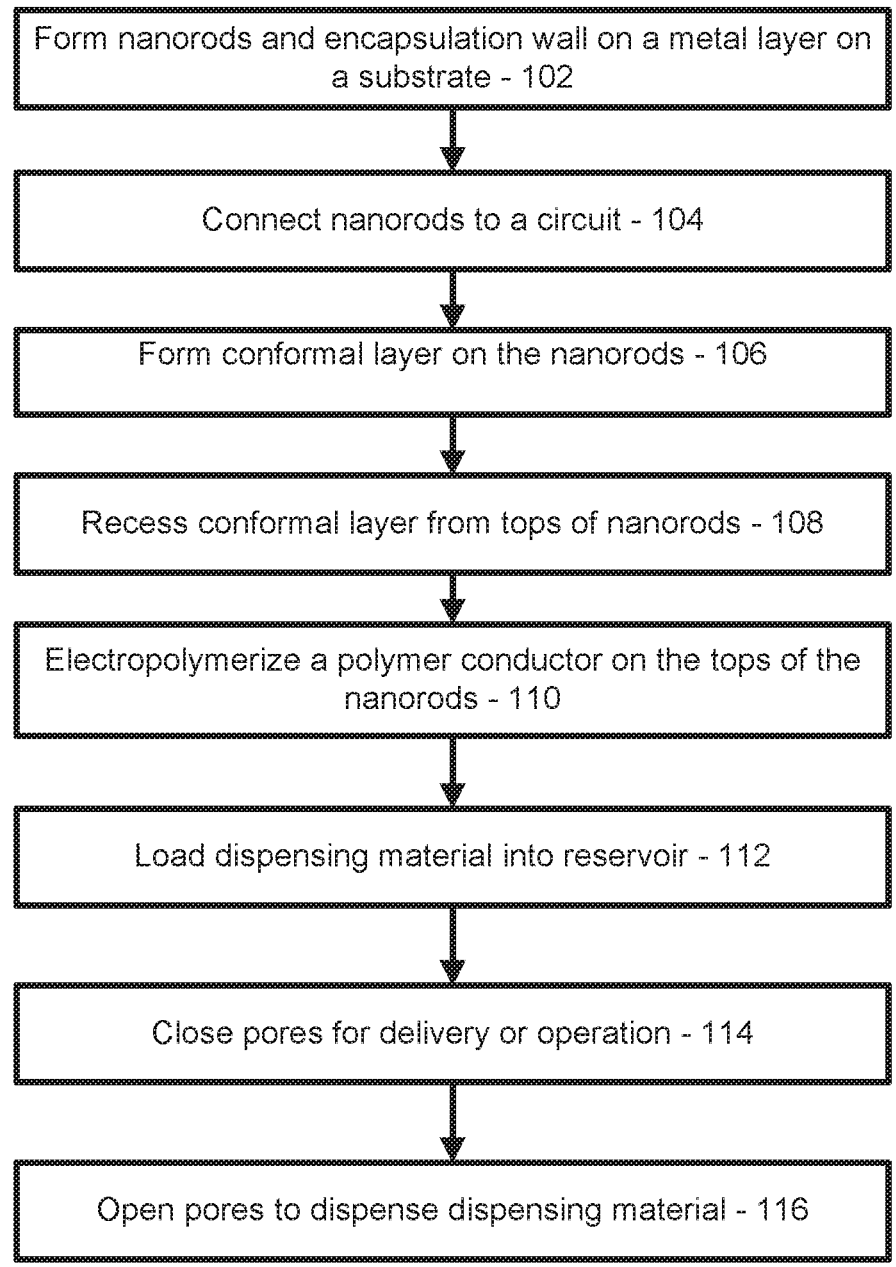
FIG. 18 is a block/flow diagram showing methods for fabricating biosensors in accordance with embodiments of the present invention.

Referring to FIG. 18, methods for fabricating biosensors are illustratively shown and described. In some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

In block 102, nanorods are formed on a metal layer. The metal layer on which the nanorods are formed can be patterned to provide electrical connections to the nanorods or groups of nanorods.

In block 104, the nanorods can be connected to a circuit to provide selective activation of the nanorods as electrodes. The circuit can include an integrated circuit formed within the same substrate as the nanorods are formed on. Alternately, the circuit or chip can connect or be integrated with the substrate with the nanorods. Metal paths can be formed by patterning the metal layer on which the nanorods are formed.

In block 106, a conformal layer is formed over the nanorods by, e.g., atomic layer deposition by depositing layers of aluminum or silicon and oxidizing. It should be understood that while Si and Al are preferred materials, other materials or combinations can be employed to form a coating or membrane.

In block 108, the conformal layer is recessed in at least one region (e.g., over a portion of the nanorods). This can include patterning a hardmask over a portion of the device and etching a protective layer, e.g., OPL, until tops of the coated nanorods are exposed. The expose tops are etched to remove the coating and expose the nanorods. The hard mask and OPL or other protective material can then be removed.

In block 110, a polymer conductor is electropolymerized on tops of nanorods exposed by recessing to form a reservoir between the electropolymerized conductor and the metal layer. The electropolymerized conductor includes pores that open and close responsively to electrical signals applied to the nanorods. The electropolymerized conductor can include polypyrrole, which can be doped with anions to be formed in its oxidation state.

In block 112, a dispensing material to be dispersed is loaded in the reservoir in accordance with open pores. The pores are held open by applying an electric field to the electropolymerized conductor (e.g., using nanorods). The dispensing material is applied to the device and settles through the open pores.

In block 114, the pores are closed for in vivo delivery and operation using a voltage on the nanorods. In block 116, in vivo or otherwise, the pores are opened to dispense the dispensing material in accordance with electrical signals. The electrical signals can be pulsed to provide better control of an amount of dispensing material released. The dispensing material can include a cell growth inhibitor, cell growth promoter, drug, or other materials. In one embodiment, the dispensing material can include a growth factor, such as, e.g., a neurotrophic growth factor, to stimulate the growth of stem cells, or other growth factors, such as, e.g., hormones (e.g., steroids), cytokines, or other proteins and stimulants.

The nanorods can be grouped into a first region and a second region where the first region includes the electropolymerized conductor and dispenses material using electric fields on narrowly spaced nanorods or other biofouling inhibition mechanism. A second region can include a sensing region, a cell growth region, etc. The first region can inhibit biofouling in at least first region or in both the first and second region. This can be performed intermittently or as needed. The dispensing material can be dispersed two or more times by opening and closing the pores when needed.

Having described preferred embodiments for a neurochemical sensors with inhibition of fouling on nano-electrodes (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. A method for fabricating a biosensor, comprising:
   forming nanorods on a metal layer;
   forming a conformal layer over the nanorods formed on the metal layer;
   recessing the conformal layer on at least a portion of the nanorods to expose tops of the nanorods;
   electropolymerizing a conductor on the tops of the nanorods exposed by the recessing to form a reservoir between the conductor and the metal layer, the conductor including pores that open and close responsively to electrical signals applied to the nanorods; and
   loading a dispensing material to be dispersed in the reservoir in accordance with open pores.

2. The method as recited in claim 1, further comprising closing the pores after loading the dispensing material in the reservoir for in vivo operation.

3. The method as recited in claim 2, wherein the pores can be opened to dispense the dispensing material for the in vivo operation.

4. The method as recited in claim 1, wherein the electrical signals can be pulsed to control an amount of dispensing material released.

5. The method as recited in claim 1, wherein the dispensing material includes a cell growth inhibitor or a cell growth promoter.

6. The method as recited in claim 1, wherein the conductor includes polypyrrole.

7. The method as recited in claim 1, wherein the nanorods are grouped into a first region and a second region where the first region includes the conductor and the dispensing material, and a second region includes a sensing region.

8. The method as recited in claim 7, wherein the first region inhibits biofouling in at least the first region.

9. The method as recited in claim 7, wherein the first region inhibits biofouling in the first region and the second region.

10. The method as recited in claim 1, wherein the dispensing material can be dispersed two or more times.

* * * * *